United States Patent
Jeong et al.

(10) Patent No.: US 11,690,587 B2
(45) Date of Patent: Jul. 4, 2023

(54) APPARATUS COMPRISING DATA OBTAINING UNIT AND IMAGE PROCESSING UNIT AND METHOD FOR PROCESSING X-RAY IMAGE

(71) Applicant: ELECTRONICS AND TELECOMMUNICATIONS RESEARCH INSTITUTE, Daejeon (KR)

(72) Inventors: Jin-Woo Jeong, Daejeon (KR); Yoon-Ho Song, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 151 days.

(21) Appl. No.: 17/172,549

(22) Filed: Feb. 10, 2021

(65) Prior Publication Data
US 2021/0244375 A1    Aug. 12, 2021

(30) Foreign Application Priority Data

Feb. 11, 2020  (KR) .................. 10-2020-0016577
Jan. 29, 2021  (KR) .................. 10-2021-0012757

(51) Int. Cl.
*A61B 6/00*     (2006.01)
*G06T 7/20*     (2017.01)
*G01N 23/04*    (2018.01)

(52) U.S. Cl.
CPC ............ *A61B 6/5217* (2013.01); *A61B 6/461* (2013.01); *A61B 6/486* (2013.01); *A61B 6/487* (2013.01);
(Continued)

(58) Field of Classification Search
CPC .......... A61B 6/486; A61B 6/487; A61B 6/52; A61B 6/5205; A61B 6/5211;
(Continued)

(56) References Cited

U.S. PATENT DOCUMENTS

| 5,119,409 A | 6/1992 | Nields et al. |
| 7,227,924 B2* | 6/2007 | Zhou ............... H01J 35/147 378/10 |
| 7,810,996 B1* | 10/2010 | Giphart ............... A61B 6/541 378/207 |
| 8,254,522 B2* | 8/2012 | Takagi ............... A61B 6/486 378/95 |

(Continued)

FOREIGN PATENT DOCUMENTS

| KR | 20160045524 A | 4/2016 |
| KR | 10-2016-0089647 A | 7/2016 |

(Continued)

OTHER PUBLICATIONS

Jin-Woo Jeong et al., "Adaptively variable dose-rate fluoroscopy using carbon nanotube field emitter-based digital x-ray tube", SPIE, Nov. 29, 2020.

*Primary Examiner* — Allen C. Ho
(74) *Attorney, Agent, or Firm* — Rabin & Berdo, P.C.

(57) ABSTRACT

Disclosed is an X-ray image processing apparatus including a data obtaining unit generating first to N-th images indicating an internal structure of an object and an image processing unit receiving the first to N-th images from the data obtaining unit, detecting a movement of the object, and generating a final image from the first to N-th images based on the movement of the object. The data obtaining unit actively controls an X-ray pulse irradiated based on the movement of the object.

11 Claims, 6 Drawing Sheets

(52) U.S. Cl.
CPC .......... *A61B 6/5205* (2013.01); *A61B 6/5211* (2013.01); *A61B 6/5235* (2013.01); *A61B 6/5264* (2013.01); *A61B 6/541* (2013.01); *A61B 6/542* (2013.01); *A61B 6/545* (2013.01); *G01N 23/04* (2013.01); *G06T 7/20* (2013.01); *G01N 2223/306* (2013.01); *G06T 2207/10116* (2013.01); *G06T 2207/20216* (2013.01)

(58) Field of Classification Search
CPC ... A61B 6/5217; A61B 6/5258; A61B 6/5264; A61B 6/54; A61B 6/541; A61B 6/542; A61B 6/545; A61B 6/40
USPC .......................................... 378/8, 42, 62, 95
See application file for complete search history.

(56) References Cited

U.S. PATENT DOCUMENTS

| | | | |
|---|---|---|---|
| 8,358,739 B2 * | 1/2013 | Lu | H05G 1/62 |
| | | | 378/98 |
| 8,542,794 B2 * | 9/2013 | Miyamoto | A61B 6/469 |
| | | | 250/354.1 |
| 9,301,728 B2 * | 4/2016 | Yabugami | A61B 6/504 |
| 10,455,677 B2 | 10/2019 | Kang et al. | |
| 10,548,557 B2 | 2/2020 | Lim et al. | |
| 10,566,170 B2 | 2/2020 | Jeong et al. | |
| 2011/0064201 A1 | 3/2011 | Takagi | |

FOREIGN PATENT DOCUMENTS

| | | |
|---|---|---|
| KR | 10-2016-0089976 A | 7/2016 |
| WO | 2009139206 A1 | 11/2009 |

\* cited by examiner

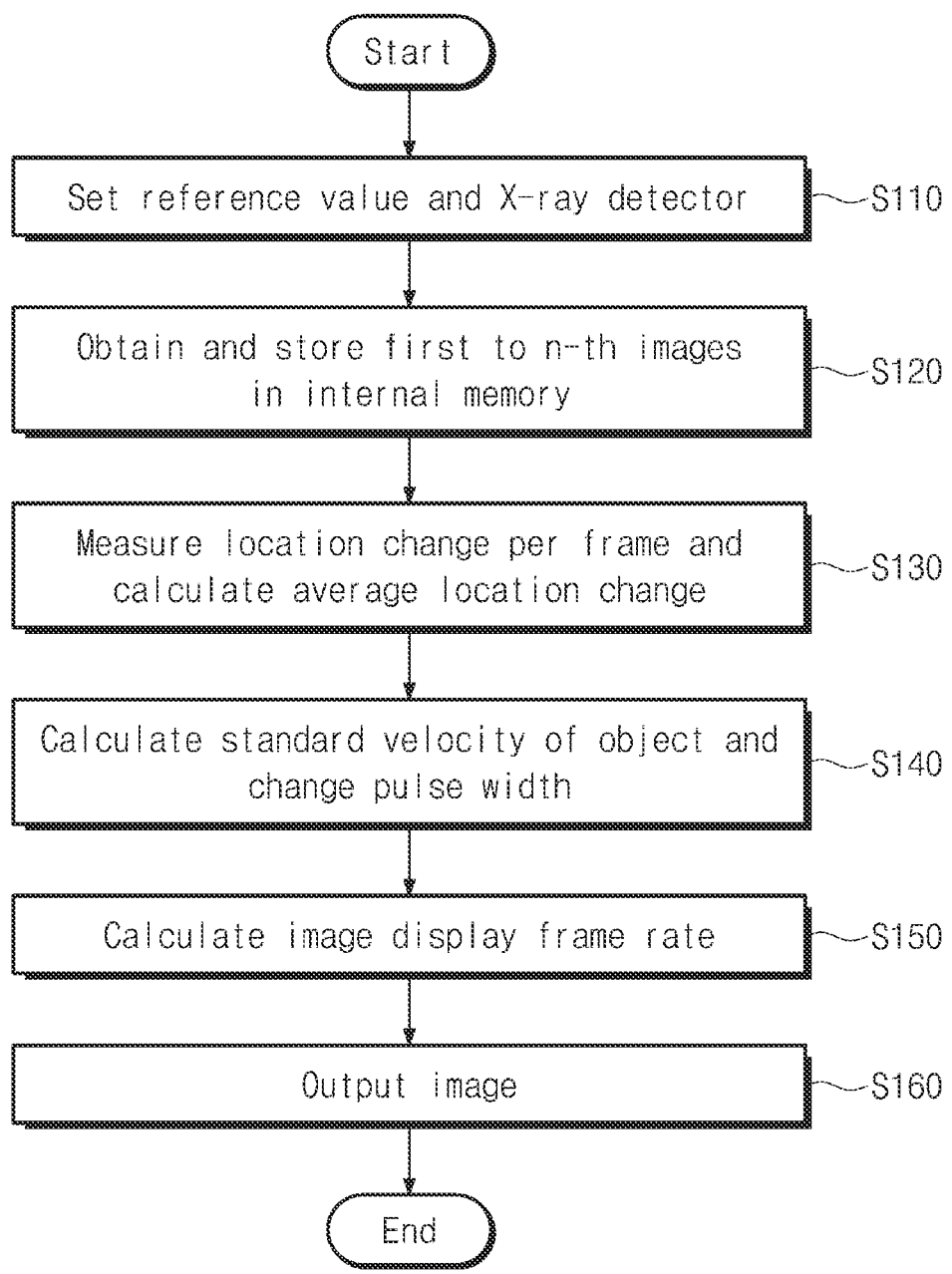

APPARATUS COMPRISING DATA OBTAINING UNIT AND IMAGE PROCESSING UNIT AND METHOD FOR PROCESSING X-RAY IMAGE

CROSS-REFERENCE TO RELATED APPLICATIONS

This application claims priority under 35 U.S.C. § 119 to Korean Patent Application No. 10-2020-0016577 filed on Feb. 11, 2020, in the Korean Intellectual Property Office, the disclosures of which are incorporated by reference herein in their entireties.

BACKGROUND

Embodiments of the present disclosure described herein relate to an image processing technology, and more particularly, relate to an X-ray image processing apparatus outputting an X-ray projection image, and a method thereof.

An X-ray imaging apparatus refers to an imaging apparatus that projects X-rays onto an object and then obtains an internal structure of the object as an image. The X-ray imaging apparatus is easily used to observe the internal structure of the object without destroying the object. As compared to other medical imaging apparatuses such as a magnetic resonance imaging (MRI) device or a computed tomography (CT) device, the X-ray imaging apparatus may obtain the internal structure image of the object within a short time. Accordingly, the X-ray imaging apparatus is widely used in food foreign object inspection, aviation security inspection, industrial non-destructive inspection, medical diagnosis, and the like. X-rays used in the X-ray imaging apparatus are radiation, and thus are harmful to a human body. Accordingly, when an X-ray imaging apparatus is used in the human body, the amount of radiation exposed to the human body needs to be minimized.

The X-ray imaging apparatus such as a C-arm used during surgery continuously irradiates X-rays to the human body to identify the projected image in real time, and thus the human body is exposed to X-rays even when the X-rays are unnecessary. In the meantime, an imaging apparatus that reduces radiation exposure by using a pulse X-ray has been recently proposed. However, the imaging apparatus has difficulty in fine-tuning the number of frames per second (FPS) and is capable of being operated manually, and thus the imaging apparatus may not respond to a movement of an object that changes in real time. Accordingly, there is a need to develop an X-ray imaging apparatus that is capable of accurately obtaining various pieces of information about an object while minimizing the number of X-ray captures and the amount of radiation exposed to a human body.

SUMMARY

Embodiments of the present disclosure provide an X-ray image processing apparatus that actively changes X-ray dose depending on the movement of an object, and a method thereof.

According to an embodiment, an X-ray image processing apparatus includes a data obtaining unit generating first to N-th images indicating an internal structure of an object and an image processing unit receiving the first to N-th images from the data obtaining unit, detecting a movement of the object, and generating a final image from the first to N-th images based on the movement of the object. The data obtaining unit actively controls an X-ray pulse irradiated based on the movement of the object.

For example, the data obtaining unit includes an X-ray irradiator irradiating an X-ray, an X-ray detector detecting an X-ray attenuated after the irradiated X-ray is irradiated to the object, generating the first to N-th images, and outputting the generated first to N-th images, and a controller controlling a pulse of the X-ray irradiated from the X-ray irradiator and controlling the X-ray detector to generate the first to N-th images.

For example, the controller controls the pulse of the X-ray based on a method of controlling at least one of amplitude of the pulse of the X-ray and a width of the pulse of the X-ray.

For example, the controller includes an internal memory storing an instruction for controlling the X-ray irradiator and the X-ray detector and a processor executing the instruction and performing a control operation on the X-ray irradiator and the X-ray detector.

For example, the X-ray detector compares a specific image among the first to N-th images with a subsequent image following the specific image to extract the movement of the object.

For example, when the movement of the object is extracted, an artificial intelligence algorithm is used.

For example, the artificial intelligence algorithm is a convolutional neural network (CNN) or a recurrent neural network (RNN).

For example, the image processing unit calculates a movement velocity of the object standardized based on a preset minimum number of display frames per second and a preset maximum number of display frames per second.

For example, the image processing unit performs an averaging or leveling operation on the first to N-th images based on a movement velocity of the object.

For example, the X-ray image processing apparatus may further include a display displaying the final image.

For example, the X-ray image processing apparatus outputs the first to N-th images as the final image when an image display frame rate is identical to a maximum number of image display frames. The X-ray image processing apparatus outputs an image obtained through an averaging operation on the first to N-th images as the final image when the image display frame rate is less than the maximum number of image display frames.

According to an embodiment, an X-ray image processing method of an X-ray image processing apparatus that actively changing an X-ray pulse includes setting a plurality of reference values for changing the X-ray pulse, obtaining first to N-th images based on the plurality of reference values, detecting a movement of an object based on the first to N-th images, calculating an image display frame rate based on the movement of the object, and outputting a final image based on the image display frame rate.

For example, the X-ray image processing method may further include modulating the X-ray pulse based on the movement of the object.

For example, the X-ray image processing method may further include comparing a specific image among the first to N-th images with a subsequent image following the specific image to extract the movement of the object.

For example, the X-ray image processing method may further include calculating a movement velocity of the object standardized based on a preset minimum number of display frames per second and a preset maximum number of display frames per second.

For example, the X-ray image processing method may further include performing an averaging or leveling operation on the first to N-th images based on a movement velocity of the object.

For example, the X-ray image processing method may further include outputting the first to N-th images as the final image when the image display frame rate is identical to a maximum number of image display frames, and outputting an image obtained through an averaging operation on the first to N-th images as the final image when the image display frame rate is less than the maximum number of image display frames.

BRIEF DESCRIPTION OF THE FIGURES

The above and other objects and features of the present disclosure will become apparent by describing in detail embodiments thereof with reference to the accompanying drawings.

FIG. 6 is a flowchart illustrating an image processing method of an X-ray image processing apparatus according to an embodiment of the present disclosure.

DETAILED DESCRIPTION

Figure 1:
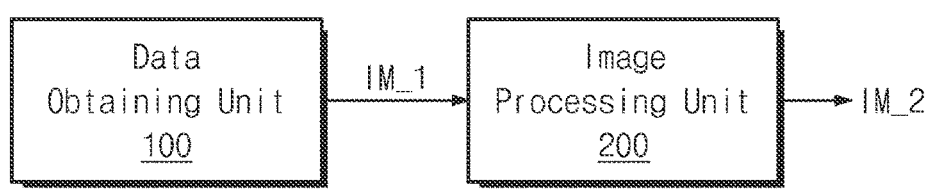
FIG. 1 is a block diagram illustrating a configuration of an X-ray image processing apparatus according to an embodiment of the present disclosure.

Hereinafter, embodiments of the present disclosure may be described in detail and clearly to such an extent that an ordinary one in the art easily implements the present disclosure.

The terms used in the specification are provided to describe the embodiments, not to limit the present disclosure. As used in the specification, the singular terms "a," "an" and "the" are intended to include the plural forms as well, unless the context clearly indicates otherwise. The terms "comprises" and/or "comprising" used herein does not exclude presence or addition of one or more other components, steps, operations, and/or elements in addition to the aforementioned components, steps, operations, and/or elements.

In the specification, the term "first and/or second" will be used to describe various elements but will be described only for the purpose of distinguishing one element from another element, not limiting an element of the corresponding term. For example, without departing the scope of the present disclosure, a first element may be referred to as a second element, and similarly, a second element may be referred to as a first element.

Unless otherwise defined, all terms (including technical and scientific terms) used in the specification should have the same meaning as commonly understood by those skilled in the art to which the present disclosure pertains. The terms, such as those defined in commonly used dictionaries, should not be interpreted in an idealized or overly formal sense unless expressly so defined herein. The same reference numerals represent the same components throughout the specification.

FIG. 1 is a block diagram illustrating a configuration of an X-ray image processing apparatus 10 according to an embodiment of the present disclosure. Referring to FIG. 1, the X-ray image processing apparatus 10 according to an embodiment of the present disclosure may include a data obtaining unit 100 and an image processing unit 200.

The data obtaining unit 100 may generate a first image IM_1 indicating an internal structure of an object by irradiating X-rays to the object. The data obtaining unit 100 may generate fundamental data for generating the first image IM_1. The fundamental data may be formed as an electrical signal indicating the X-ray detection result. The data obtaining unit 100 may output the first image IM_1 to the image processing unit 200. Detailed components and operating principles of the data obtaining unit 100 will be described in detail with reference to FIG. 2 to be described later.

The image processing unit 200 may generate a second image IM_2, which is an output image indicating the internal structure of the object, based on the first image IM_1 input from the data obtaining unit 100. The image processing unit 200 may perform operations of processing, converting, and analyzing the first image IM_1 to generate the second image IM_2. Although not illustrated in FIG. 1, the image processing unit 200 may include an internal memory and a processor that executes instructions.

The processor included in the image processing unit 200 may include a graphic processing unit (GPU) for graphics processing. The processor may be implemented as a System on Chip (SoC) in which a core and a GPU are integrated with each other. The processor may include a single core, dual cores, triple cores, quad cores, and multi cores. The processor may execute instructions to perform operations of processing, converting, and analyzing the first image IM_1.

The internal memory included in the image processing unit 200 may include a random access memory (RAM) that stores signals or data input from the outside of the X-ray image processing apparatus 10 or is used as a storage area for various operations performed by the X-ray image processing apparatus 10. Furthermore, the internal memory included in the image processing unit 200 may include a read only memory (ROM) that stores a control program for controlling the X-ray image processing apparatus 10 and instructions executed by the processor.

Operations of the image processing unit 200 of processing, converting, and analyzing the first image IM_1 will be described in detail with reference to FIG. 4 to be described later. Moreover, although not illustrated in FIG. 1, the X-ray image processing apparatus 10 according to an embodiment of the present disclosure may further include a display for displaying the second image IM_2 generated by the image processing unit 200.

Figure 2:
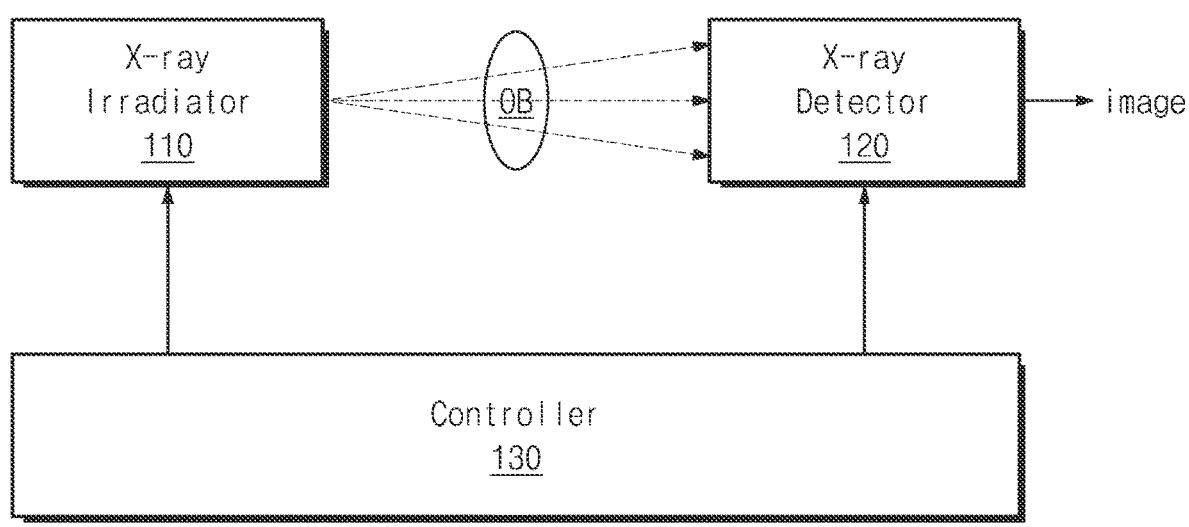
FIG. 2 is a block diagram illustrating a configuration of a data obtaining unit according to an embodiment of the present disclosure.

FIG. 2 is a block diagram illustrating a configuration of the data obtaining unit 100 according to an embodiment of the present disclosure. Referring to FIG. 2, the data obtaining unit 100 may include an X-ray irradiator 110, an X-ray detector 120, and a controller 130. An object OB illustrated in FIG. 2 is illustrated for convenience of description, and is not illustrated as a component of the data obtaining unit 100.

The X-ray irradiator 110 may generate X-rays and may irradiate the X-rays to the object OB. Although not illustrated in FIG. 2, the X-ray irradiator 110 may include an X-ray source that generates X-rays and a collimator that adjusts an X-ray irradiation area. The X-ray irradiator 110 may generate X-rays by applying a high voltage between a cathode and an anode of a vacuum tube that is internally included. The intensity of an X-ray output from the X-ray irradiator 110 may vary depending on an X-ray tube voltage, an X-ray tube current, and a pulse shape that are applied to the vacuum tube.

The X-ray detector 120 may detect X-rays that are irradiated from the X-ray irradiator 110 and then are projected onto the object OB. X-rays output from the X-ray irradiator 110 may be attenuated while passing through the object OB. The X-ray detector 120 may detect the attenuated X-rays to generate the first image IM_1 indicating the internal structure of the object OB. In detail, the X-ray detector 120 may convert the attenuated X-rays into an electrical signal and may generate the first image IM_1 based on the converted signal. The X-ray detector 120 may output the generated first image IM_1 to the image processing unit 200 (see FIG. 1).

The controller 130 may control operations performed by the data obtaining unit 100 to generate the first image IM_1. For example, the X-ray irradiator 110 and the X-ray detector 120 may perform an operation of irradiating and detecting X-rays for generating the first image IM_1 under control of the controller 130. Furthermore, the controller 130 may control the X-ray irradiator 110 and the X-ray detector 120 to generate the first image IM_1 based on the X-ray detection result of the X-ray detector 120.

Although not illustrated in FIG. 2, the controller 130 may include an internal memory and a processor that executes instructions. The processor included in the controller 130 may include a GPU for graphics processing. The processor may be implemented as an SoC in which a core and a GPU are integrated with each other. The processor may include a single core, dual cores, triple cores, quad cores, and multi cores. The processor may execute instructions to perform a control operation on the X-ray irradiator 110 and the X-ray detector 120.

The internal memory included in the controller 130 may include a RAM that stores signals or data input from the outside of the X-ray image processing apparatus 10 or is used as a storage area for various operations performed by the X-ray image processing apparatus 10. Furthermore, the internal memory included in the controller 130 may include a ROM that stores a control program for controlling the X-ray irradiator 110 and the X-ray detector 120 and instructions executed by the processor.

In X-ray image processing, when there is a movement of the object OB, it is necessary to adjust FPS of an X-ray projection image. For example, when the object OB does not move, it is necessary to properly adjust the amount of X-rays irradiated per hour by decreasing FPS of the X-ray projection image. When the object OB moves faster, it is necessary to properly adjust the amount of X-rays irradiated per hour by increasing FPS of the X-ray projection image. X-ray dose may be determined by an X-ray tube voltage, an X-ray tube current, a pulse width of an X-ray, and a pulse period of the X-ray. In an embodiment according to the present disclosure, the controller 130 may irradiate X-rays to the object OB by actively adjusting the X-ray dose output from the X-ray irradiator 110 based on the movement of the object OB. A method of adjusting X-ray dose by the controller 130 will be described in detail with reference to FIG. 3 to be described later.

Figure 3:
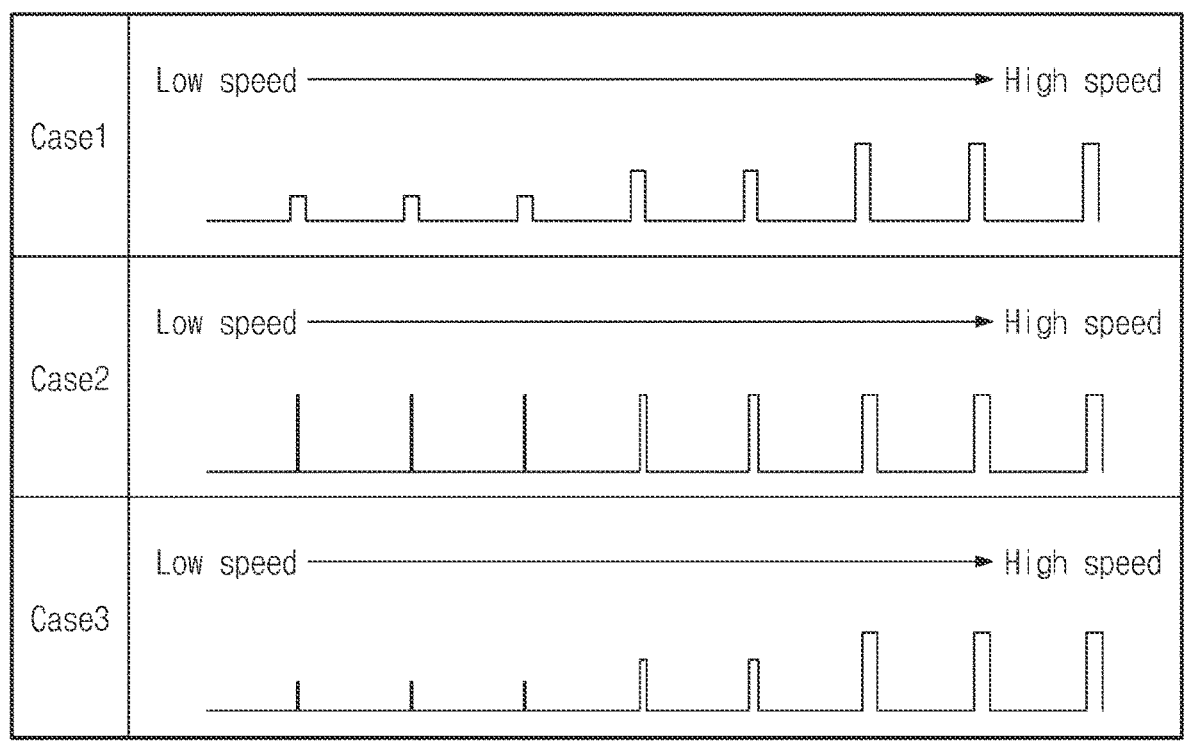
FIG. 3 is a diagram illustrating a method of controlling X-ray dose according to an embodiment of the present disclosure.

FIG. 3 is a diagram illustrating a method of controlling X-ray dose according to an embodiment of the present disclosure. In more detail, case1 of FIG. 3 discloses a method (a pulse amplitude modulation (PAM)) of controlling by changing a tube current, that is, the amplitude of a pulse although a pulse width of an X-ray is constant. case2 of FIG. 3 discloses a method (a pulse width modulation (PWM)) of controlling a tube current by changing a pulse width of the X-ray although the tube current is uniform. case3 of FIG. 3 discloses a method (PAM+PWM) of controlling both the tube current and the pulse width.

The dose of an X-ray irradiated from the X-ray irradiator 110 (see FIG. 2) may be determined depending on an X-ray tube voltage, an X-ray tube current, a pulse width of an X-ray, and a pulse period of the X-ray. The dose of an X-ray may increase as the tube voltage and the tube current increase, as the pulse width increases, and as the pulse period decreases. In particular, the FPS of the X-ray image processing apparatus 10 (see FIG. 1) may be changed when the dose is controlled by changing the period of a pulse.

According to the PAM scheme disclosed in case1 of FIG. 3, the controller 130 (see FIG. 2) controls X-rays such that the tube current is changed in proportion to a movement velocity of the object OB (see FIG. 2). That is, the controller 130 decreases the tube current as the movement of the object OB is slow. The controller 130 increases the tube current as the movement of the object OB is fast. According to the PWM scheme disclosed in case2 of FIG. 3, the controller 130 controls X-rays such that the pulse width is changed in proportion to a movement velocity of the object OB. That is, the controller 130 decreases the pulse width as the movement of the object OB is slow. The controller 130 increases the pulse width as the movement of the object OB is fast. According to the 'PAM+PWM' scheme disclosed in case3 of FIG. 3, the controller 130 controls X-rays such that the tube current and the pulse width are changed in proportion to a movement of the object OB. That is, the controller 130 decreases the tube current and the pulse width as the movement of the object OB is slow. The controller 130 increases the tube current and the pulse width as the movement of the object OB is fast.

Although not illustrated in FIG. 3, in the 'PAM+PWM' method, the controller 130 decreases the tube current and increases the pulse width when the movement of the object OB is slow; and the controller 130 increases the tube current and decreases the pulse width when the movement of the object OB is fast. In the case where the controller 130 decreases the pulse width when the movement of the object OB is fast, it may prevent image blur due to the movement. On the other hand, the controller 130 may increase the tube current, thereby preventing dose from being reduced.

The X-ray dose control method disclosed in FIG. 3 may be classified into three types, but these are only some embodiments. For example, various X-ray dose control methods may be used. For example, the X-ray dose may be controlled by a method of controlling dose by a tube voltage. According to an embodiment of the present disclosure, the controller 130 may control the X-ray irradiator 110 based on one of various X-ray dose adjustment methods, and thus the X-ray image processing apparatus 10 may adjust the irradiated X-ray dose.

Figure 4:
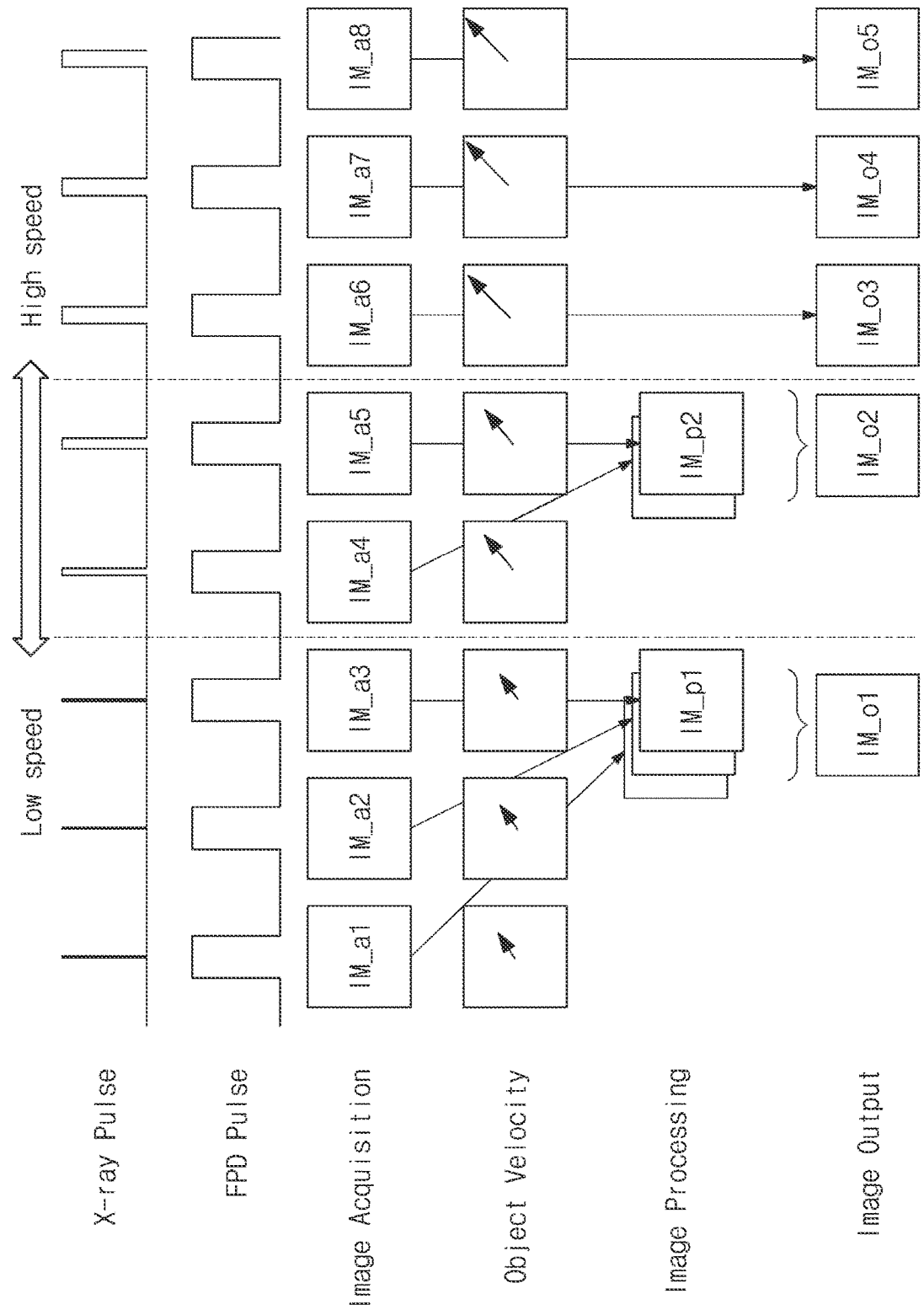
FIG. 4 is a diagram illustrating an operating principle of an X-ray image processing apparatus according to an embodiment of the present disclosure.

FIG. 4 is a diagram illustrating an operating principle of the X-ray image processing apparatus 10 (see FIG. 1) according to an embodiment of the present disclosure. In FIG. 4, an embodiment according to a method of controlling X-ray dose based on a method of changing a pulse width depending on a movement of the object OB (see FIG. 2) is disclosed. According to the method of changing a pulse width depending on the movement of the object OB, the X-ray image processing apparatus 10 finally changes FPS.

At this time, the variable degree of X-ray dose is referred to as an adaptively variable dose-rate (AVD).

The X-ray detector 120 (see FIG. 2) of the X-ray image processing apparatus 10 according to an embodiment of the present disclosure may obtain X-ray images IM_a1, IM_a2, . . . , and, IM_a8 based on a maximum FPS, may detect the movement of the object OB, and may output final images IM_o1, IM_o2, . . . , and IM_o5 based on the detected movement of the object OB. When the object OB is stopped, the X-ray image processing apparatus 10 may average a plurality of low-dose images obtained by minimizing the X-ray dose and may output the averaged images IM_p1 and IM_p2. In this case, although the FPS is small, the final images IM_o1, IM_o2, . . . , and, IM_o5 with the minimized noise may be output.

According to an embodiment of the present disclosure, when the movement of the object OB is detected, the X-ray image processing apparatus 10 may increase the dose of an X-ray, may reduce the number of images that are targets to be averaged, and may increase the FPS to be suitable for the reduced the number of images. In this case, when the movement of the object OB is maximized, the final image may be output at the maximum FPS without averaging images.

According to the embodiment of the present disclosure disclosed in FIG. 4, the X-ray image processing apparatus 10 may periodically obtain an X-ray image and may output the final image through image processing. For example, when the maximum FPS is 30, the X-ray image processing apparatus 10 may obtain an X-ray image at a period of about 33.3 ms and may output the final image through image processing. At this time, the X-ray dose may be changed depending on the movement of the object OB, and thus the number of averaging frames of the obtained image is changed. Accordingly, the number of frames in an image finally output may be variable. However, the finally-output image is an image having the same signal-to-noise ratio, and an image having the same quality may be displayed.

The X-ray image processing apparatus 10 may set a tube voltage kV, a tube current mA, a minimum pulse width MinW, a maximum pulse width MaxW, a maximum subject location change per frame MaxPPF, and the minimum number of display frames per second $DFPS_{min}$, and the maximum number of display frames per second $DFPS_{max}$, and may perform a gain correction of the X-ray detector 120 with the set tube voltage, the set tube current, and the set maximum pulse width. The image obtained for each frame from the X-ray detector 120 may be compared with an image at the previous frame to extract a movement $PPF_i$ of the object OB at the corresponding frame.

Because the extracted motion of the object OB is not accurate due to noise when a low-dose image is obtained, the X-ray image processing apparatus 10 may measure the movement of an object by using the average of several frames, that is, N frames. At this time, the X-ray image processing apparatus 10 may calculate a movement velocity OV of the object OB (or having a value of 0 at standstill and a value of 1 at maximum velocity) that is standardized based on the preset minimum number of display frames per second and the preset maximum number of display frames per second. The movement velocity of the object OB may be calculated by an artificial intelligence algorithm. A deep learning technology such as convolutional neural network (CNN) and recurrent neural network (RNN) may be used for the artificial intelligence algorithm. The pulse width, the image display frame rate (DFPS), and the number of average frames (NAF) may be calculated based on the value of the movement velocity of the object OB by using Equation 1 to Equation 3.

$$W \text{ (Pulse width)} = (MaxW - MinW) \cdot OV + MinW \qquad \text{[Equation 1]}$$

$$DFPS \text{ (Image display frame rate)} = 1 + 29 \cdot OV \qquad \text{[Equation 2]}$$

$$NAF \text{ (Number of average frames)} = 30 - 29 \cdot OV \qquad \text{[Equation 3]}$$

The image processing unit 200 (see FIG. 1) may perform an image processing operation of generating a final output image on an image obtained based on an X-ray pulse and FPS. For example, the image processing operation may include an averaging or leveling operation. In the image processing operation, various parameters such as a pulse width, a DFPS, and an NAF may be used to generate a final image.

In FIG. 4, for convenience of description, an embodiment according to a method of controlling X-ray dose based on a method of changing a pulse width depending on the movement of the object OB (see FIG. 2) in a situation where the tube voltage, the tube current, and the pulse period are constant is disclosed. The tube voltage and the tube current may vary depending on the movement of the object OB to efficiently control X-ray dose.

Figure 5:
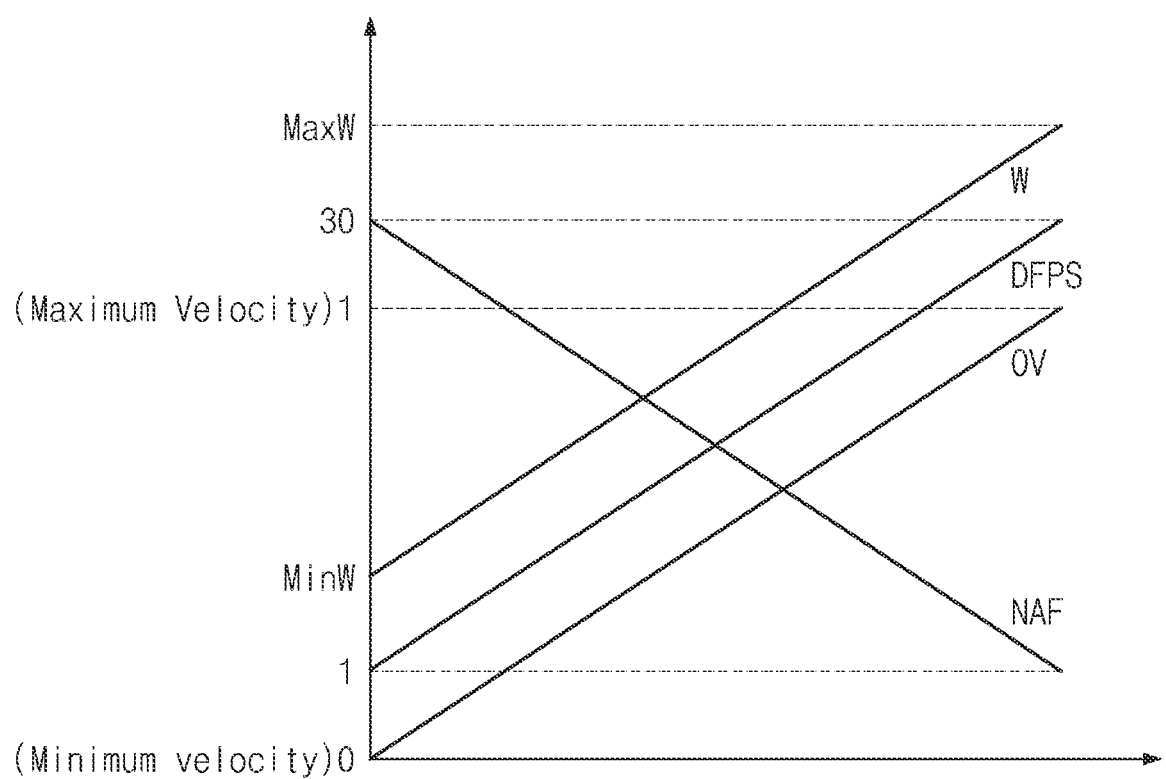
FIG. 5 is a diagram illustrating a correlation between parameters used in an X-ray image processing apparatus according to an embodiment of the present disclosure.

FIG. 5 is a diagram illustrating a correlation between parameters used in an X-ray image processing apparatus (see FIG. 1) according to an embodiment of the present disclosure.

When a movement velocity OV of the object OB increases because the movement of the object OB (see FIG. 2) increases, the number of display frames per second may increase up to the maximum number of display frames per second $DFPS_{max}$. When the movement velocity OV of the object OB decreases, the number of display frames per second may decrease to the minimum number of display frames per second $DFPS_{min}$. For example, the maximum number of display frames per second $DFPS_{max}$ may have a value of 30. The minimum number of display frames per second $DFPS_{min}$ may have a value of 1. The calculated pulse width W may be delivered to the X-ray irradiator 110 (see FIG. 2) for the next frame image, and thus the pulse width of an X-ray may be changed.

When the calculated DFPS is the maximum number of display frames per second $DFPS_{max}$, the previously-obtained frame is output as it is. Otherwise, an image is output by averaging several frames depending on the DFPS. For example, when the DFPS is calculated as 15, the final image may be output as an image having 15 frames per second by averaging respective 2 images among obtained 30 images per second. Also, when the DFPS is 1, an image having 1 frame per second may be output by averaging 30 images.

The parameters disclosed in FIG. 5 are illustrated to have values linearly proportional to the movement of the object OB. However, this is only an example. For example, the parameters do not necessarily have to be linear. In other words, the parameters may have various function relationships, such as logarithmic, exponential, and polynomial, for effective image display.

FIG. 6 is a flowchart illustrating an image processing method of an X-ray image processing apparatus (see FIG. 1) according to an embodiment of the present disclosure. Hereinafter, descriptions the same as the above-described contents will be omitted to avoid redundancy.

In operation S110, the X-ray image processing apparatus 10 may set a reference value and the X-ray detector 120 (see FIG. 2). For example, the reference value may include the tube voltage kV, the tube current mA, the minimum pulse width MinW, the maximum pulse width MaxW, the maximum subject location change per frame MaxPPF, the minimum number of display frames per second $DFPS_{min}$, and the maximum number of display frames per second $DFPS_{max}$. The X-ray image processing apparatus 10 may perform a gain correction of the X-ray detector 120 (see FIG. 2) by using the set tube voltage, the set tube current, and the set maximum pulse width.

In operation S120, the X-ray image processing apparatus 10 may obtain first to n-th images based on various parameters set in operation S110 and may store the obtained first to n-th images in an internal memory. The number of frames of the obtained first to n-th images may be based on the set FPS.

In operation S130, the X-ray image processing apparatus 10 may extract the movement of the object OB in the corresponding frame, that is, a location change of the object OB, by comparing the image obtained for each frame with an image at the previous frame. The location change of the object OB may be extracted by an artificial intelligence algorithm. A deep learning technology such as CNN and RNN may be used for the artificial intelligence algorithm. Besides, the X-ray image processing apparatus 10 may calculate an average position change of the entire plurality of frames based on location changes per frame.

In operation S140, the X-ray image processing apparatus 10 may calculate the movement velocity OV of the object OB that is standardized based on the preset minimum number of display frames per second and the preset maximum number of display frames per second. In addition, the X-ray image processing apparatus 10 may change the pulse width of the X-ray by reflecting the result of calculating the movement velocity OV of the object OB.

In operation S150, the X-ray image processing apparatus 10 may calculate a DFPS and an NAF. When the movement velocity OV of the object OB increases because the movement of the object OB increases, the number of image display frames may increase up to the maximum number of display frames per second $DFPS_{max}$. When the movement velocity OV of the object OB decreases, the number of image display frames may decrease up to the minimum number of display frames per second $DFPS_{min}$.

In operation S160, the X-ray image processing apparatus 10 may output a final image based on the DFPS and the NAF. When the calculated DFPS is the maximum number of display frames per second $DFPS_{max}$, the previously-obtained frame is output as it is. Otherwise, an image is output by averaging several frames depending on the DFPS. When the final image is output, the procedure ends.

Figure 7A:
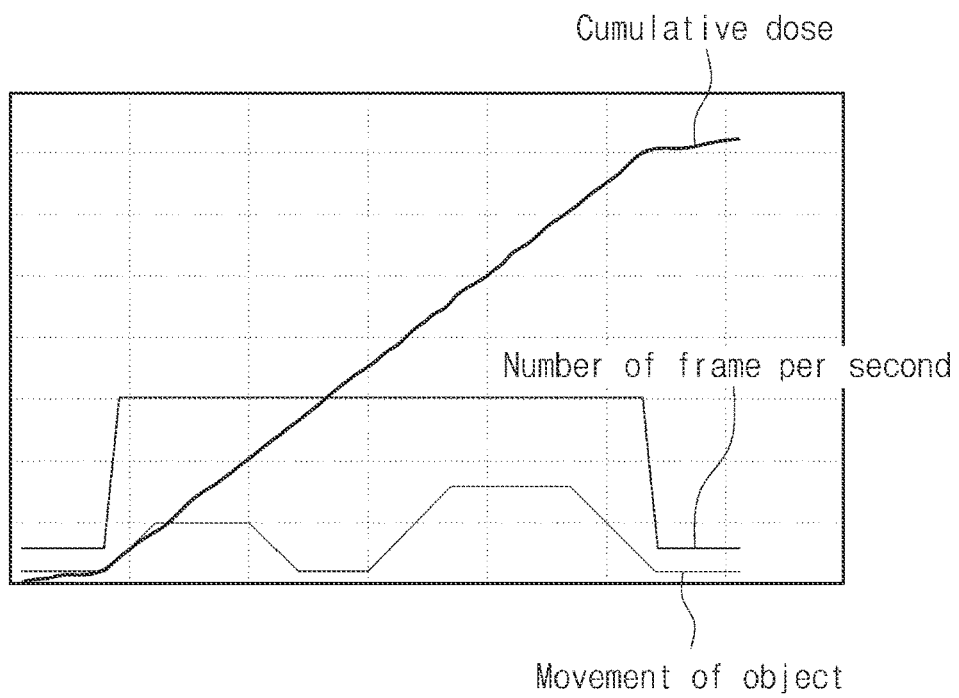
FIGS. 7A and 7B are diagrams illustrating X-ray cumulative dose according to movement of an object.
Figure 7B:
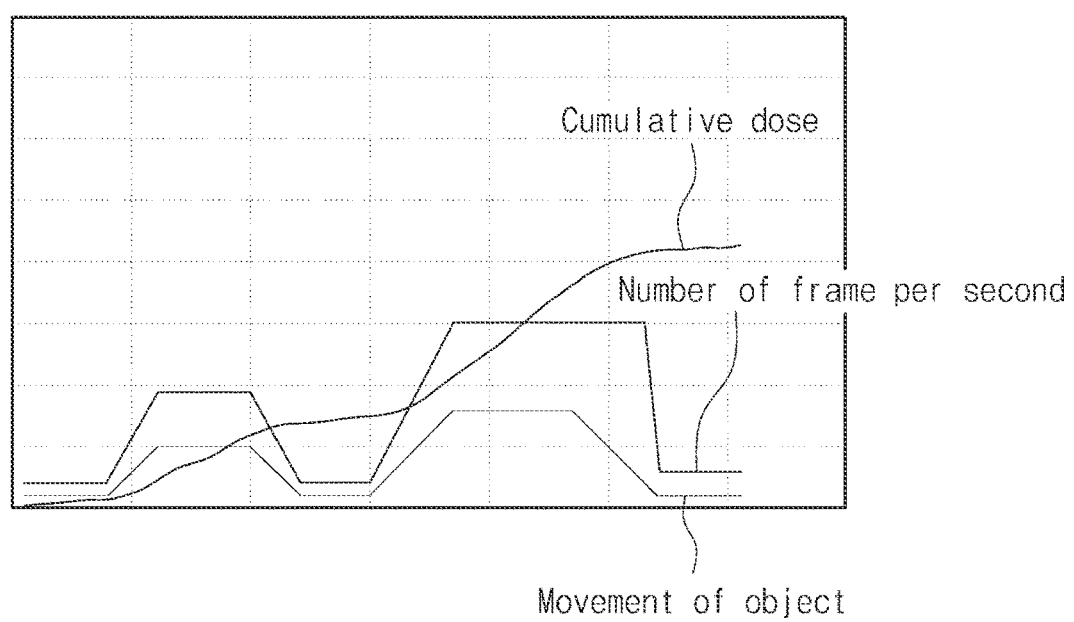

FIGS. 7A and 7B are diagrams illustrating X-ray cumulative dose according to movement of an object OB (see FIG. 2). In more detail, FIG. 7A illustrates an accumulated amount of X-rays when an FPS is manually adjusted depending on a movement of the object OB. FIG. 7B illustrates an accumulated amount of X-rays when an FPS is actively adjusted depending on a movement of the object OB by an active variable X-ray image processing apparatus (see FIG. 1) according to an embodiment of the present disclosure.

Referring to FIG. 7A, because the FPS is capable of being set within a limited range, the FPS needs to be maintained at a specific level even when the movement of the object OB is fast or slow. Accordingly, the cumulative amount of X-rays increases as time goes on.

In the meantime, referring to FIG. 7B, as compared to a case where the FPS is constant, the cumulative X-ray dose is reduced by actively changing the FPS. In particular, more X-ray doses may be reduced when the movement of the object OB is changed rapidly (e.g., when a standstill situation occurs frequently). Besides, when the X-ray control principle according to the present disclosure is applied to a field emitter-based digital X-ray source, the tube current and a pulse shape may be changed instantly and quickly, and thus the amount of radiation exposure may be reduced effectively.

The above-mentioned description refers to embodiments for implementing the scope of the present disclosure. Embodiments in which a design is changed simply or which are easily changed may be included in the present disclosure as well as an embodiment described above. In addition, technologies that are easily changed and implemented by using the above embodiments may be included in the present disclosure. While the present disclosure has been described with reference to embodiments thereof, it will be apparent to those of ordinary skill in the art that various changes and modifications may be made thereto without departing from the spirit and scope of the present disclosure as set forth in the following claims.

In accordance with an X-ray image processing apparatus and method according to an embodiment of the present disclosure, unnecessary radiation exposure to an object may be prevented by actively controlling X-ray dose depending on the movement of an object.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. An X-ray image processing apparatus comprising:
a data obtaining unit configured to generate first to N-th images indicating an internal structure of an object; and
an image processing unit configured to:
receive the first to N-th images from the data obtaining unit;
detect a movement of the object; and
generate a final image from the first to N-th images based on the movement of the object,
wherein the data obtaining unit actively controls a pulse of an X-ray irradiated based on the movement of the object;
wherein the image processing unit performs an averaging operation or a leveling operation on the first to N-th images based on a movement velocity of the object.

2. The X-ray image processing apparatus of claim 1, wherein the data obtaining unit includes:
an X-ray irradiator configured to irradiate the X-ray;
an X-ray detector configured to detect an X-ray attenuated after the irradiated X-ray is irradiated to the object, to generate the first to N-th images, and to output the generated first to N-th images; and
a controller configured to control the pulse of the X-ray irradiated from the X-ray irradiator and to control the X-ray detector to generate the first to N-th images.

3. The X-ray image processing apparatus of claim 2, wherein the controller controls the pulse of the X-ray based on a method of controlling at least one of an amplitude of the pulse of the X-ray and a width of the pulse of the X-ray.

4. The X-ray image processing apparatus of claim 2, wherein the image processing unit calculates the movement velocity of the object standardized based on a preset minimum number of display frames per second and a preset maximum number of display frames per second.

5. The X-ray image processing apparatus of claim 1, further comprising:
a display configured to display the final image.

6. The X-ray image processing apparatus of claim 1, wherein the image processing unit is configured to output the final image by processing the first to N-th images when an image display frame rate is identical to a maximum number of image display frames, and
wherein the image processing unit is configured to output the final image by processing an image obtained through an averaging operation on the first to N-th images when the image display frame rate is less than the maximum number of image display frames.

7. An X-ray image processing method, the method comprising:
setting a plurality of reference values for changing an X-ray pulse;
obtaining first to N-th images based on the plurality of reference values;
detecting a movement of an object based on the first to N-th images;
calculating an image display frame rate based on the movement of the object;
performing an averaging operation or a leveling operation on the first to N-th images based on a movement velocity of the object; and
outputting a final image based on the image display frame rate.

8. The X-ray image processing method of claim 7, further comprising: modulating the X-ray pulse based on the movement of the object.

9. The X-ray image processing method of claim 7, further comprising: comparing a specific image among the first to N-th images with a subsequent image following the specific image to extract the movement of the object.

10. The X-ray image processing method of claim 7, further comprising:
calculating the movement velocity of the object standardized based on a preset minimum number of display frames per second and a preset maximum number of display frames per second.

11. The X-ray image processing method of claim 7, wherein the outputting the final image based on the image display frame rate includes:
outputting the final image by processing the first to N-th images when the image display frame rate is identical to a maximum number of image display frames, and
outputting the final image by processing an image obtained through an averaging operation on the first to N-th images-when the image display frame rate is less than the maximum number of image display frames.

* * * * *